United States Patent [19]

Cole et al.

[11] Patent Number: 5,342,777

[45] Date of Patent: Aug. 30, 1994

[54] CELL CULTURE MEDIUM FOR HUMAN LIVER EPITHELIAL CELL LINE

[75] Inventors: Katharine H. Cole, Dayton; John F. Lechner; Curtis C. Harris, both of Bethesda, all of Md.

[73] Assignee: The United States of America as represented by the Secretary of the Dept. of Health and Human Services, Washington, D.C.

[21] Appl. No.: 844,873

[22] Filed: Mar. 3, 1992

Related U.S. Application Data

[63] Continuation of Ser. No. 284,331, Dec. 14, 1988, abandoned.

[51] Int. Cl.$^5$ .......... C12N 1/00; C12N 5/00; C12N 15/00; C12Q 1/00
[52] U.S. Cl. .......... 435/240.31; 435/4; 435/172.3; 435/240.2; 435/948
[58] Field of Search .......... 435/4, 6, 172.3, 240.2, 435/240.31, 948

[56] References Cited

U.S. PATENT DOCUMENTS

| | | |
|---|---|---|
| Re. 30,985 | 6/1982 | Cartaya .......... 435/240.31 |
| 3,073,746 | 1/1963 | Thompson et al. . |
| 3,882,233 | 5/1975 | Grant et al. . |
| 4,757,005 | 7/1988 | Chan . |
| 4,885,238 | 12/1989 | Reddel et al. . |

OTHER PUBLICATIONS

Lescoat et al, "Influence of Ornithine on Allumin Synthesis by Fetal and Neonatal Hepatocytes Maintained in Culture", Biol. Abs. 84(6) #57462, Sep. 15, 1987.

Van Zoelen et al, "Phenotypic Transformation of Normal Rat Kidney Cells in a Growth-Factor-Defined Medium: Induction by a Neuroblastomane-Derived Transforming Growth Factor Independently of the Epidermal Growth Factor Receptor", Biol. Abs. v. 80(3) Aug. 1, 1985 #23,550.

Hoshi et al, "Production of an Auto-Stimulatory Growth Factor by Human Hepatoma Cells Abrogates Requirement for a Brain-Derived Factor" in: *Growth and Differentiation of Cells in Defined Environment* ed: Murakami et al., pp. 281–284, 1985.

Kaighn et al, "Growth Control of Prostatic Cells in Serum Free Media Interrelationships of Hormone Response Cell Density and Nutrient Media", PNAS V. 78, 5673–5676, 1981.

Lechner et al, "Clonal Growth of Normal Adult Bronchial Epithelial Cells in a Serum-Free Medium", In Vitro, V18, 633–642, 1982.

Ledley et al., "Retrovial Gene Transfer into Primary Hepatocytes: Implications for Genetic Therapy of Liver-Specific Functions", PNAS, v. 84, 5335–5339, Aug., 1987.

Reid, "Cloning", Methods in Enzymology, V. LVIII, 152–164, 1979.

Miles Laboratories, Inc., "ExCyte" Brochure, 1986.

*Primary Examiner*—Robert J. Hill, Jr.
*Assistant Examiner*—Gian P. Wang
*Attorney, Agent, or Firm*—Birch, Stewart, Kolasch & Birch

[57] ABSTRACT

The present invention relates to cell medium developed to support long term multiplication and permanent establishment of a cell line of human liver epithelial cells. The medium may contain an effective cell growth promoting amount of calcium ions; an effective cell growth promoting amount of glucose; an effective amount of insulin to aid cells in glucose uptake; an effective cell growth promoting amount of hydrocortisone; an effective amount of epidermal growth factor to bind epidermal growth factor receptors on cells; an effective amount of transferrin to increase DNA synthesis in cells; an effective amount of cholera toxin to increase DNA synthesis in cells; an effective amount of triiodothyronine to increase DNA synthesis in cells; and an effective growth promoting amount of mammalian hormones and mitogenic factors, including lipoprotein, cholesterol, phospholipids and fatty acids.

15 Claims, No Drawings

CELL CULTURE MEDIUM FOR HUMAN LIVER EPITHELIAL CELL LINE

This application is a continuation of application Ser. No. 07/284,331, filed on Dec. 14, 1988, now abandoned.

CROSS REFERENCE TO RELATED APPLICATIONS

This application is related to Ser. No. 07/284,368 filed on Dec. 14, 1988 concurrently herewith entitled HUMAN LIVER EPITHELIAL CELL LINE, which is hereby incorporated by reference.

BACKGROUND OF THE INVENTION

The culture of hepatocytes represents a valuable approach for studying specific mechanisms of xenobiotic metabolism, chemical carcinogenesis, as well as pathology related to inherent or induced metabolic or biochemical abnormalities. Cultures of human hepatocytes can provide a more relevant view of human liver metabolism and disease processes than data obtained from hepatocyte cultures derived from other animal species.

Several problems have hindered in vitro studies of human hepatocytes. One problem is the availability of viable, normal adult human liver. In the past several years we have been involved with the development of an immediate autopsy program which has allowed us to obtain adult human liver tissue within 1 hr following death from patients free of liver disease.

Another problem associated with culture of human hepatocytes, as with most differentiated cells, is that these cells rarely divide in culture. By modifying a serum-free culture medium that was shown to support longterm multiplication of liver epithelial cells from Rhesus monkeys, we have developed replicative cultures of adult human liver cells. However, as with all normal cells, these liver epithelial cells eventually undergo senescence in culture.

The present invention is related to serum-less culture medium (denatured serum) for growth of continuous and non-continuous cell lines. More particularly the present invention is related to culture medium for liver epithelial cells with extended life spans.

The human liver is one of the few organs in adult man capable of regeneration. However, cultures of adult hepatocytes have never been adequately established. Those that have been established are only viable for a limited period of time and are produced in insufficient quantities for research in pharmacology, chemotherapy or oncogenesis.

There are several examples of animal liver cell cultures derived from experimental laboratory animals such as rats (Tsao et. al., Exp. Cell Res. 154: 38–52 (1984); Enat et al., "Proc. Nat. Acad. Sci. USA" 87: 1411–1415 (1984)) but these are not suitable for long term studies due to the limited life span of the culture.

Rat liver cells have been transformed by transfection with SV40 DNA (Woodworth et al, Cancer Res. 46: 4018–4026 (1987); Ledley et al., "Proc. Nat. Acad. Sci. USA" 84: 5335–5339 (1987)) but they are not suitable for human drug metabolism or carcinogenesis studies because of xenobiotic metabolism differences between rat and human liver cells. Further Woodworth reports that immortalized cell lines did not arise spontaneously. Woodworth points out that exposure to hormones and mitogenic factors, in particular EGF, insulin and glucogan, serum factors and virus infection stimulate hepatocyte DNA synthesis.

Clonally-derived cultures of human hepatocytes have been reported (Kaighn and Prince, Proc. Nat. Acad. Sci., 68, 2396–2400 (1971)), but no new data has been generated to support or refute these observations. In addition the medium used contained 17% serum. Several studies have shown that serum (Hashi and Cart J. Cell Physiol., 125, 82–90 (1985)), and more specifically transforming growth factor-beta (TGF-$\beta$) present in serum (Nakaruma et al., Biochem Biophys Res Commu., 133 1042-50 (1985); Lin et al., Biochem. Biophys. Res. Commu., 143, 26–30 (1987); and Strain et al., Biochem. Biophys. Res. Commu., 145, 436–442 (1987)) cause a marked decrease in DNA synthesis of rat hepatocytes in culture.

Rat liver epithelial cells from adult rat liver tissue have been established using serum free medium (Chessebeuf and Padieu In Vitro, 20, 780–795 (1984); Enat et al. Proc. Natl. Acad. Sci., 81, 1411-1415, (1984)).

Human hepatoma cell lines have been cultured and are available (e.g. Knowles et al., U.S. Pat. No. 4,393,133, Jul. 12, 1983, Human Hepatoma Derived Cell Line) but, are not usable in carcinogenesis studies because they are tumorigenic. They were also cultured in medium containing serum.

As is known in the art, the field of tissue culture medium is empirical in nature, and there is little or no predictability as to whether conditions developed for one species will be operable in another.

SUMMARY OF THE INVENTION

It is, therefore, an object of the present invention to provide an improved aqueous culture medium to produce a normal human liver epithelial cell line that is prolific, enduring and has an unlimited life span in culture. As a result, it has been found that a suitable basic culture medium which provides nutrients may be modified with the addition of insulin, epithelial growth factor (EGF), hydrocortisone, transferrin, cholera toxin, aqueous bovine pituitary extract (Lechner, J. and Laveck, M. J., J. Tissue Cult. Method 9, 43–48 (1985)), denatured serum and HepG2 conditioned medium (Hoshi, H. and McKeehan, W. L. In Vitro Cell Dev. Biol., 21:125–128 (1985)) accomplishes the intended result. The medium described herein contains chemically denatured serum that contains no active TGF-$\beta$.

It is a further object of the invention to produce a cell culture medium containing ornithine, fatty acids, insulin, EGF, hydrocortisone, transferrin, cholera toxin, aqueous pituitary extract and denatured serum added to commercially available PFMR4 medium (without arginine), conditioned with medium from HepG2 hepatoma cells for liver cell lines which can be used in experiments that require large numbers of homogenous (identical and cloned) cells for: drug metabolism studies; evaluating chemical compounds which require liver metabolism for functional activation; chemical carcinogenesis studies with the potential for screening compounds with human carcinogenic and or tumor promoting potential; investigation of controls of differentiation for possible use with anti-liver cancer drugs which act by inducing terminal differentiation; growth of Hepatitis virus in replicating hepatocytes; growth of human parasites; and transfection of additional oncogenes to evaluate their effect on these cells.

It is a further object of the invention to provide a culture medium for an "continuous" cell line, i.e. that grow continually without senescence when cultured in vitro in a suitable medium. These and other objects, features and advantages of the invention will be better understood upon a reading of the following detailed description of the invention.

The above objects of the invention have been substantially achieved by the development of an improved serum free culture medium. The culture medium is prepared using the basal medium PFMR4 (described in Lechner et al. Methods in Cell Biol., 21, 195 (1980)) with arginine, calcium, glutamine, trace elements and iron not included.

The mammalian cell culture medium of the present invention may contain an effective cell growth promoting amount of calcium ions; an effective cell growth promoting amount of glucose; an effective amount of insulin to aid cells in glucose uptake; an effective cell growth promoting amount of hydrocortisone; an effective amount of epidermal growth factor to bind to epidermal growth factor receptors on cells; an effective amount of transferrin to increase DNA synthesis in cells; an effective amount of cholera toxin to increase DNA synthesis in cells; an effective amount of triiodothyronine to increase DNA synthesis in cells; and an effective growth promoting amount of mammalian hormones.

In a more preferred embodiment of the invention the mammalian cell culturing medium contains an effective cell growth promoting amount of the essential amino acids; an effective cell growth promoting amount of water soluble vitamins; an effective cell growth promoting amount of coenzymes; an effective cell growth promoting amount of sodium ions; an effective cell growth promoting amount of calcium ions; an effective cell growth promoting amount of glucose; an effective amount of insulin to aid cells in glucose uptake; an effective cell growth promoting amount of hydrocortisone; an effective amount of epidermal growth factor to bind epidermal growth factor receptors on cells; an effective amount of transferrin to increase DNA synthesis in cells; an effective amount of cholera toxin to increase DNA synthesis in cells; an effective amount of triiodothyronine to increase DNA synthesis in cells; an effective amount of retinoic acid to increase DNA synthesis in cells; and an effective growth promoting amount of mammalian hormones.

In a most preferred embodiment of the invention the cell culturing medium is an aqueous cell culturing medium suitable for culturing normal adult human liver epithelial cells which contains water; an effective cell growth promoting amount of all of the essential amino acids; an effective cell growth promoting amount of water soluble vitamins; an effective cell growth promoting amount of coenzymes; an effective cell growth promoting amount of sodium ions; an effective amount of calcium ions high enough to promote cell growth but low enough to avoid cellular differentiation; an effective cell growth promoting amount of glucose; insulin in an amount of 1 to 10 $\mu$g/ml; hydrocortisone in an amount of 0.05 to 1 $\mu$M; epidermal growth factor in an amount of 1 to 25 ng/ml; transferrin in an amount of 1 to 10 $\mu$g/ml; cholera toxin in an amount of 5 to 50 ng/ml; triiodothyronine in an amount of 1 to 100 nM; retinoic acid in an amount of 1 to 300 nM; an effective amount of a mammalian pituitary extract to provide hormones necessary for culturing normal adult human liver epithelial cells; an effective cell growth promoting amount of conditioned medium derived from HepG2 hepatoblastoma cells or a mutant thereof; and an effective amount of a buffer to maintain the pH between 6.7 and 7.6.

The glucose is a energy source for the cells and is preferably present in an amount of 0.5 to 0.5 mg/ml. Insulin should also be included in an amount sufficient to aid the cells in glucose uptake. This amount is preferably 1 to 10 $\mu$g/ml.

The hydrocortisone, cholera toxin and retinoic acid are potentially toxic and therefore should be present in amounts sufficient to achieve their desired effects, but low enough not to inhibit cell growth due to the inherent toxicity of these materials.

The epidermal growth factor, transferrin, cholera toxin, triiodothyronine, retinoic acid and bovine pituitary extract aid DNA synthesis. Mitogenic factors should be present in an amount sufficient to aid DNA synthesis.

The pH of the culturing medium may be adjusted to achieve an optimal effect depending on the cell line to be cultured. The pH is usually between 6.7 and 7.6, preferably 7.0 and 7.4, more preferably 7.1 to 7.3, and most preferably about 7.2.

The bovine pituitary extract is present in an amount sufficient to provide the necessary hormones for cell growth. The bovine pituitary extract may be present in an amount of 0.75 to 75 $\mu$g/ml.

The culture medium should contain a source of an aqueous mixture of lipoprotein, cholesterol, phospholipids and fatty acids with low endotoxin. A suitable source of these ingredients is EX-CYTE® V sold by Miles Inc., Miles Diagnostics.

The Ex-cyte products including V have the following characteristics:

Animal virus and mycoplasma free.

Certification of freedom from animal viruses and mycoplasma available.

All components heat-treated equivalent to 10 hr. at 60° C.

Contains no IgG or IgM.

Water soluble.

Low level of endotoxin.

Stable for years at −20 degrees C. EX-CYTE® products are unique aqueous (or water soluble) lipoprotein fractions that cause the modulation of cell membrane proteins. They are a mixture of lipoprotein cholesterol, phospholipids, and fatty acids and consequently are a source of lipids the cells can use to design membrane structure and optimize surface protein positioning. Idealized protein orientation can enhance membrane receptor accessibility and permeability of solutes. In addition, by supplying the cells with the preformed cholesterol and phospholipids, the cells need not biosynthesize the lipids from base ingredients such as exogenous fatty acids. Fortification with the transport proteins, albumin and transferrin, provides cells with many of the factors required for growth with basal media. The fatty acids are an energy source for liver cells for DNA synthesis when the cells start to divide.

The Ex-cyte products have the following general composition:

TABLE III

CHARACTERISTICS

Lipoprotein Profile of EX-CYTE

| Bovine Cholesterol | Triglycerides | Cholesterol | Human Triglycerides |
| --- | --- | --- | --- |

TABLE III-continued

CHARACTERISTICS

| | (mg/mL) | (mg/mL) | (mg/mL) | (mg/mL) |
|---|---|---|---|---|
| Total: | 9.48 | 0.05 | 5.24 | 2.87 |
| VLDL: | 0 | 0 | 0.40 | 1.07 |
| LDL: | 3.36 | 0.03 | 4.80 | 1.78 |
| HDL: | 6.12 | 0.02 | 0.04 | 0.02 |

Phospholipid Profile of EX-CYTE

| | Bovine | Human |
|---|---|---|
| Total Phospholipids, mg/mL | 10.53 | 5.54 |
| Phosphatidyl Choline, mg/mL | 7.15 | 2.49 |
| Lysophosphatidyl Choline, mg/mL | 0.93 | 0.69 |
| Sphingomyelin, mg/mL | 2.34 | 2.36 |
| Phosphatidyl Ethanolamine, mg/mL | 0.02 | 0 |
| Total Cholesterol, mg/mL | 9.48 | 5.24 |
| Cholesterol, Phospholipid Ratio | 0.90 | 0.95 |

Free Fatty Acid Analysis of EX-CYTE

| | Bovine |
|---|---|
| Total Cholesterol | 15.2 mg/mL |

| Fatty Acid | Approx. Conc. µg/ml | µg fatty acid/ mg cholesterol |
|---|---|---|
| Linoleic, C 18:2 | 546 | 35.9 |
| Palmitic, C 16 | 233 | 15.3 |
| Oleic, C 18:1 | 156 | 10.3 |
| Stearic, C 18 | 348 | 22.9 |

The EX-CYTE should be present in an amount of 100 to 1500 µg/ml, preferably 150 to 500 µg/ml, most preferably about 312 µg/ml.

A broad spectrum antibiotic such as gentamicin and antimycotic agents may be included in the culture medium to prevent bacterial, yeast, fungal or other contamination.

Normal human adult liver cells are cultured at a density sufficient to allow cell growth. Typical concentrations are $5 \times 10^1$ to $1 \times 10^4$ cells/cm$^2$ of surface area of the cell culture container, preferably $5 \times 10^2$ to $3 \times 10^3$ cells/cm$^2$, most preferably about $1\,3 \times 10^3$ cells/cm$^2$. The cells are cultivated under moist aerobic conditions at a temperature between 33° to 40° C., preferably about 37° C. The cell culture is passaged as the cells approach confluence on the surface on which they are being cultured. The normal human adult liver cells can be cultured for at least two rounds of DNA synthesis, preferably at least five rounds of DNA synthesis and more preferably at least 10 rounds of DNA synthesis. Transformed cells can be cultured under much less restrictive or controlled conditions.

The present invention is also directed to a method for culturing various types of mammalian cells, including normal adult human liver epithelial cells as well as other types of human cells, which comprises culturing the cells in the above-described culturing medium.

DETAILED DESCRIPTION OF THE INVENTION

The above and other objects and advantages of the present invention are achieved by human liver epithelial cell line continually growing when cultured in vitro in the growth medium. Unless defined otherwise, all technical and scientific terms used herein have the same meanings commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

The term "immortalized" as used herein means that the cell line grows continually without senescence when cultured in vitro in a suitable growth medium.

The successful culturing of liver epithelial cells in the medium of the present invention results from the unexpected finding that ornithine, fatty acids, insulin, EGF, hydrocortisone, transferrin, cholera toxin, aqueous pituitary extract and denatured serum and conditioned with HepG2 medium to provide factors necessary in the successful proliferation of liver cells.

General Method for Preparation of the Basic Medium

Basal PFMR4 medium prepared is as described in Lechner, J. F. et al. Normal human prostate epithelial cell cultures are described in Harris, C. C., Trump B. F., Stoner G. D. (eds) Methods in Cell Biology, Vol. 21B, Academic Press, New York, pp 195–225.

The basal medium was supplemented with additives previously listed.

ILLUSTRATIVE EXAMPLES OF THE INVENTION

It is, of course, to be understood that the following examples are for purposes of illustration only and that numerous alterations may be made in the components, precise proportions and conditions set forth herein without departing from the spirit of the invention as defined in the appended claims.

EXAMPLE I (PREPARATION OF MEDIUM)

The medium was prepared in three steps. Step 1 was the preparation, by a commercial source of "basic medium" which contains the basic nutrients and some other components. The second step was the addition to the medium of various key ingredients and salts which if included in the "basic medium" when prepared by the commercial source would curtail the shelf life of the product. Therefore step 2 is usually conducted only shortly before the medium is to be used. The third step was the conditioning of the medium on certain cells to extract factors which are essential for the medium.

The medium is formulated in accordance with good laboratory procedure as known in the art.

TABLE I

1. Basic Medium

The formula is as follows:

A custom basal medium PFMR4 (Lechner et al. Methods in Cell Biol., 21, 195 (1980)) is commercially available from facilities such as Biological Research Faculty & Facility, Inc., Ijamsville, MD 21754. The custom medium used omitted certain ingredients specified in Lechner, above e.g. arginine (has been taken out of the base medium because fibroblasts present in the original isolation cannot live without arginine and so the culture becomes almost totally hepatocytes), calcium (has been used at different concentrations so it is not added into the original medium), glutamine (left out due to shelf life degradation of the glutamine), trace elements and iron (tend to precipitate out of solution after long periods of time so they are added fresh). The main reason for the omission is to obtain a longer shelf life for the "basic medium."

The custom basal medium contains:

| INGREDIENT | mg/liter |
|---|---|
| Essential Amino Acids | |
| L-Cystine.2HCl | 47.0 |
| L-Histidine | 41.9 |
| L-Isoleucine | 7.9 |
| L-Leucine | 26.2 |
| L-Lysine.HCl | 73.0 |

TABLE I-continued

| | |
|---|---|
| L-Methionine | 9.0 |
| L-Phenylalanine | 9.9 |
| L-Threonine | 23.8 |
| L-Tryptophan | 4.1 |
| L-Tyrosine.2Na.2H$_2$O | 15.7 |
| L-Valine | 23.4 |
| Nonessential Amino Acids | |
| L-Alanine | 17.8 |
| L-Asparagine.H$_2$O | 30.0 |
| Aspartic Acid | 26.6 |
| Glutamic Acid | 29.4 |
| L-Glycine | 15.0 |
| L-Proline | 69.1 |
| L-Serine | 21.0 |
| or derivatives | |
| Amino Acid Derivatives | |
| Putrescine.2HCl | 0.32 |
| Water Soluble Vitamins and Coenzymes | |
| d-Biotin | 0.07 |
| Folic Acid | 1.32 |
| DL-A-Lipoic Acid (Thioctic) | 0.21 |
| Nicotinamide | 0.04 |
| D-Pantothenic Acid | 0.24 |
| Pyridoxine.HCl | 0.06 |
| Riboflavin | 0.04 |
| Thiamine.HCl | 0.34 |
| Vitamin B12 (Cynacobalamine) | 1.36 |
| Carbohydrate/Derivatives | |
| Pyruvic Acid | 174.0 |
| Sodium Acetate | 295.6 |
| Nucleic Acid Derivatives | |
| Hypoxanthine | 4.1 |
| Thymidine | 0.7 |
| Lipids/Derivative | |
| Choline Chloride | 14.0 |
| i-Inositol | 18.0 |
| Bulk Inorganic Ions (Salts) | |
| NaCl | 5844.0 |
| KCl | 283.3 |
| Na$_2$HPO$_4$ | 126.4 |
| KH$_2$PO$_4$ | 58.5 |
| MgSO$_4$ | 19.3 |
| MgCl$_2$.6H$_2$O | 105.7 |
| Inorganic Trace Elements | |
| CuSO$_4$.5H$_2$O | 0.002 |
| Buffers and Indicators | |
| NaHCO$_3$ | 1176.0 |
| HEPES buffer (Made by Biofluids) | 7149.0 |
| Phenol Red | 1.1 |

TABLE II

2. Additional Substances

To the commercial medium the following substances were added to bring the final concentration to the indicated concentrations:

| Item | Amount |
|---|---|
| L-glutamine | 2 mM |
| insulin | 10 μg/ml |
| hydrocortisone | 0.2 μM |
| epidermal growth factor | 5.0 ng/ml |
| transferrin | 10 μg/ml |
| phosphoethanolamine | 0.5 μM |
| cholera toxin | 25 ng/ml |
| triiodothyronine | 10 nM |
| retinoic acid | 10 nM |
| ornithine | 2 mM |
| CaCl$_2$ | 0.4 mM |
| glucose | 2.0 mg/ml |
| bovine pituitary extract | 7.5 μg/ml |
| "Ex-cyte ® V (Miles Diagnostics, Pentex Products Kankakee, IL) | 312 μg/ml |
| FeSO$_4$.7H$_2$O | 2.7 μM |
| ZnSO$_4$.7H$_2$O | 0.5 μM |
| Factor Free Serum | 10% |
| (Van Zoolen et al., J Cell Phvsiol., 123: 151 (1985)) | |
| Na$_2$SeO$_3$ | 3.0 × 10$^{-8}$M |
| MnCl$_2$.4H$_2$O | 1.0 nm |
| Na$_2$SiO$_3$.9H$_2$O | 5.0 × 10$^{-7}$M |
| (NH$_4$)$_6$ Mo$_7$O$_{24}$.4H$_2$O | 1.0 nM |
| NH$_4$VO$_3$ | 5.0 nM |
| NiSO$_4$.6H$_2$O | 0.5 nM |
| SnCl$_2$.2H$_2$O | 0.5 nM |
| Gentamicin | 50 μg/ml |

Unless otherwise indicates, the quantities may be varied by a factor of 1 log or plus or minus 20% depending on toxic effect of the ingredient at higher levels and minimal requirements for growth; which modifications are considered to be "about" those required to function as does the listed formula.

The Serum free medium (growth-factor-inactivated serum) was prepared as follows: Fetal bovine serum (FBS; Flow Laboratories, Irvine, Scotland) was incubated with 100 mM dithiothreitol (DTT; Boehringer, Mannheim, GFR) for 2 hr at room temperature while stirring, resulting in turbid solution. The suspension was then dialyzed (molecular weight cutoff 8–10 kDa) overnight at 4° C. against a 50–100 fold excess of phosphate-buffered saline without Ca$^{++}$ and Mg$^{++}$ (PBS; 137 mM NaCl, 2.7 mM KCl, 6.5 mM Na$_2$HPO$_4$, 1.5 him KH$_2$PO$_4$, pH 7.4). Subsequently iodoacetamide (Sigma, St. Louis, Mo., USA) was added at 5 g/liter, and the suspension incubated for another 2 hr at room temperature while stirring, followed by dialysis for 2 days against several aliquots of PBS, and an additional day against PBS containing in addition 0.9 mM CaCl$_2$ and 0.5mM MgCl$_2$. Subsequently the SH-FCS was centrifuged at 25,000 g for 30 min at 4° C., and the supernatant again at 100,000 g for 60 min at 4° C. The clear supernatant was sterilized by passage through a Millex-GV 0.22 nm filter (Millipore, Bedford Mass., USA). (Prepared from protocol in Van Zoelen et al *J. Cell Physiol.*, 123, 151–160 (1985)).

The Ex-cyte ® used had the following characteristics

| PENTEX ® EX-CYTE ® V, 50X Growth Enhancement Media Supplement Albumin Enriched (Salt Poor) | |
|---|---|
| PROTEIN By Biuret | 786 mg/g powder |
| CHOLESTEROL (1) By Enzymatic Assay | 64.3 mg/g powder |
| SODIUM CHLORIDE | 5.0 mg/g |
| pH (7% Solution) | 7.9 mg/g |
| ENDOTOXIN LEVEL By Limulus Amebocyte Lysate | 0.03 ng/mg |
| MOISTURE By Karl Fischer | Less than 5% when packaged |
| STORAGE | −20° C. or below |
| RECONSTITUTE WITH (2) | Pyrogen-free H$_2$O or redissolve directly in nutrient medium |

(1) It has been previously determined that there is approximately a 1:1 ratio of phospholipids and cholesterol in EX-CYTE preparations.
(2) 625 mg of powder is sufficient for one liter of final nutrient medium containing 40 μg cholesterol/mL and 0.49 mg albumin/mL. Endotoxin level at working concentration of cholesterol and albumin is 0.02 ng/mL.

The conditioned medium is prepared by placing the HGM medium on medium density monolayer cultures of 1) HepG2 hepatoblastoma cells (American Type Tissue Collection #HB80-65) or 2) Human liver epithelial cells transformed by transfection with SV-40 DNA (NCI/NIH, patent pending) for 72 hours. This conditioned medium is added to normal HGM at a 35% concentration.

EXAMPLE 2 (TRANSFECTED CELLS)

Development of HLC-Cell Line

Normal human hepatocytes were isolated from immediate autopsy tissue from non-cancerous individuals by a 2O combination of perfusion and digestion techniques as described by Hsu et al, *In Vitro Cell Develop. Biol.*, 21:154-160 (1985). The left lobe of the liver was removed from non-cancerous patients within 2 hr of cessation of cardiac function, immersed in ice cold Lebowitz-15 cell medium (L-15) and transported to the site of liver cell isolation.

The hepatocytes were dissociated into cell suspensions by perfusing the liver with a calcium and magnesium free Hank's balanced salt solution containing 0.5 mM EDTA, and 0.05M Hepes at 37° C., at a flow rate of 30–40 ml/min for 15 min.

The perfusate was then changed to a digestion solution containing collagenase (185–200 U/ml) at 37° C. at a flow rate of 30–40 ml/min for 20 min. The dissociated hepatocytes were purified from debris and red blood cells by 3 successive washes with L-15 and filtration through a 10μ nylon filter The hepatocytes were suspended in Waymouth's medium supplemented with 10% fetal bovine serum (FBS), 1 μg/ml insulin and 50 μg/ml gentamicin. The yield estimated counting the cells with a hemocytometer were $1-2\times10^7$ cells/g of liver tissue. Over 90% of the hepatocytes excluded trypan blue.

Following isolation the cells (hepatocytes) were seeded into T-75 tissue culture flasks (Lux, Miles Scientific. Naperville, Ill.) whose surfaces had been coated with collagen (Michalopoulos, G. and Pitot, *H. Exp Cell Res.*, 94:70–73 (1975) (Flow Lab, Rockville, Md.) at $3-5\times10^5$ cells/flask using Waymouth's cell medium with insulin (1 μg/ml), gentamicin (50 μg/ml), and fetal bovine serum (10%).

Twenty-four hours after initial seeding, the medium was changed to serum-free medium HGM (Hepatocyte Growth Medium) PFMR4 described below. The medium made without arginine and supplemented with ornithine (2 mM), insulin (10 μg/ml), hydrocortisone (0.2 μM), epidermal growth factor (5 ng/ml), transferrin (10 μg/ml), phosphoethanolamine (0.5 μM), cholera toxin (25 ng/ml), triiodothyronine (10 nM), bovine pituitary extract (7.5 μg/ml) and factor-free serum (10%). Additionally, this medium was supplemented (35%) with conditioned medium obtained by placing medium described above in contact with high density cultures of human hepatoblastoma cell line (HepG2) for 72 hrs.

Forty-eight hours after the original isolation and 3 hours prior to transfection the cells were fed with 10 ml of LHC-9 cell medium (Lechner, J. F. and Laveck, M. A. *Tissue Cult. Method,* 9:43–48 (1985). The cells were transfected with a plasmid pRSV-T (obtained from NCI), which contained SV40 ori-construction containing the SV40 early region genes and the Rous sarcoma virus long terminal repeat (LTR). Transfection was accomplished by using the strontium phosphate coprecipitation method described by Brash, D. et al, *Molec. Cell Biol.*, 7:2031-2034 (1987).

$3-5\times10^5$ cells/flask (T-75 cm) were transfected with 10 μg of DNA precipitate at pH 7.8. After two hours of exposure, the hepatocytes were rinsed twice with serum-free cell medium at 37° C. prior to glycerol shock (15% glycerol for 3 minutes).

Two weeks following transfection, the cells were passaged. Thereafter, upon confluence the cells were passaged twice more. The appearance of transformed colonies occurred 6–8 weeks following original transfection in passage 3 at a frequency of $1\times10^{-4}$. The transformed colonies primarily contained epithelial looking cells, however, the morphology of cells in the foci was variable, some cells having a fibroblastic appearance.

Attempts to clone single cells or loci from the original cultures resulted in death of the cells within 2–3 days. Thereafter, the flasks were serially passaged. The first two passages following foci appearance were passaged using the collagenase/Dispase solution used for original isolation due to the extreme sensitivity of the cells to trypsin. The remaining passages were done with a PVP-trypsin-EGTA solution. With increasing passage, the cells became more homogeneous, and at the 5th passage following transfection, virtually 100% of the cells expressed SV40 large T antigen.

With increasing passage the cells became more homogenous and at passage 8 virtually all the cells expressed SV40 large T antigen (as determined by indirect immunofluorescence), as well as cytokeratin 18 (a cytokeratin known to be expressed in normal human hepatocytes (Moll, R. W. et al, *Cell,* 31:11-24 (1982)).

All subsequent culture of the liver epithelial cells was in HGM, and these cells continued to proliferate for about 14 weeks at which time the culture senesced (i.e., entered crisis). Currently, 3 months after the cells entered crisis, colonies of dividing cells are present but have not been characterized.

To establish the expression of SV40 large T antigen cells from passage 3 were grown on culture chamber slides and using indirect immunofluorescence, the culture was found to contain approximately 30% T antigen positive cells. By passage 5, the transformed liver cells were found to be uniformly positive for T antigen as determined by immunofluorescence. T antigen expression was maintained throughout subsequent culturing.

To establish that these transformed liver cells were epithelial, cells from early and late passages were examined for keratin expression using a general cytokeratin primary antibody and a fluorescent secondary antibody and found to be uniformly positive in both early (p.3) and late (p.11) passages.

Further examination using monoclonal antibodies against cytokeratin 18 and 19 was performed. At early and late passage the liver cells were positive for cytokeratin 18 but negative for cytokeratin 19. However, in late passages (p.10 and 11) some cells became positive for cytokeratin 19 as well as 18.

We examined the transformed liver epithelial cells for the production of proteins that are expressed by normal hepatocytes. The transformed cells were analyzed using fluorescent immunocytochemistry for expression of albumin, alpha 1 antitrypsin and alpha 2 macroglobulin. Albumin was detected in several colonies on the slide. Overall, approximately 20% of the cells taken from passage 9 were positive for albumin expression. When the cells were exposed to serum containing medium for 48 hrs prior to staining, more cells were positive for albumin expression (30–40%).

Materials used in this example include Dispase (0.5 U/mg) obtained from Boehringer Mannheim (Indianapolis, Ind.), collagenase (156 U/mg) from Worthington Biochemical Corp. (Freehold, N.J.) and standard tissue culture media and components from Biofluids Inc. (Rockville, Md.). Epidermal growth factor from Collaborative Research Inc. (Bedford, Mass.). Trypsin inhibitor, DNase and chemicals from Sigma Chemical Co. (St. Louis, Mo.) PFMR4 cell culture medium and factor free serum were prepared by Biological Research Faculty and facility (Ijamsville, Md.). Ex-cyte V ® (Miles Laboratories, Diagnostics Division) a bovine lipoprotein, was used as a source of lipoprotein cholesterol, phospholipids and fatty acids with low endotoxin.

Serum free medium (growth-factor-inactivated serum) was prepared as follows: Fetal calf serum (FCS; Flow Laboratories, Irvine, Scotland) was incubated with 100mM dithiothreitol (DTT; Boehringer, Mannheim, GFR) for 2 hr at room temperature while stirring, resulting in turbid solution. The suspension was then dialyzed (molecular weight cutoff 8–10 kDa) overnight at 4° C. against a 50–100 fold excess of phosphate-buffered saline without $Ca^{++}$ and $Mg^{++}$ (PBS; 137 mM NaCl, 2.7 mM KCl, 6.5MM $Na_2HPO_4$, 1.5 mM $KH_2PO_4$, pH 7.4). Subsequently iodoacetamide (Sigma, St. Louis, Mo., USA) was added at 5 g/liter, and the suspension incubated for another 2 hr at room temperature while stirring, followed by dialysis for 2 days against several aliquots of PBS, and an additional day against PBS containing in addition 0.9 mM $CaCl_2$ and 0.5 mM $MgCl_2$. Subsequently the SH-FCS was centrifuged at 25,000 g for 30 min at 4° C., and the supernatant again at 100,000 g for 60 min at 4° C. The clear supernatant was sterilized by passage through a Millex-GV 0.22 nm filter (Millipore, Bedford Mass., USA). Prepared from protocol in Van Zoelen et al, *J. Cell Physiol.*, 123: 151–160 (1985)

The final serum-free medium (Lechner et al. *Methods in Cell Biol.* 21, p. 195, 1980) was prepared without arginine, calcium, glutamine, trace elements and iron. The medium was supplemented with:

| | |
|---|---|
| L-glutamine | 2 mM |
| insulin | 10 µg/ml |
| hydrocortisone | 0.2 µM |
| epidermal growth factor (Collaborative Research Inc. Bedford Mass.) | 5.0 ng/ml |
| transferrin | 10 µg/ml |
| phosphoethanolamine | 0.5 µM |
| cholera toxin | 25 ng/ml |
| triiodothyronine | 10 nM |
| retinoic acid | 10 nM |
| ornithine | 2 mM |
| $CaCl_2$ | 0.4 mM |
| glucose | 2.0 mg/ml |
| bovine pituitary extract | 7.5 µg/ml |
| "Ex-cyte" ® V (Miles Diagnostics, Pentex Products Kankakee, IL) | 312 µg/ml |
| $FeSO_4.7H_2O$ | 2.7 uM |
| $ZnSO_4.7H_2O$ | 0.5 uM |
| Factor Free Serum (Van Zoolen et al., J Cell Physiol., 123: 151 (1985)) | 10% |
| $Na_2SeO_3$ | $3.0 \times 10^{-8}$ M |
| $MnCl_2.4H_2O$ | 1.0 nm |
| $Na_2SiO_3.9H_2O$ | $5.0 \times 10^{-7}$ M |
| $(NH_4)_6 Mo_7O_{24}.4H_2O$ | 1.0 nM |
| $NH_4VO_3$ | 5.0 nM |
| $NiSO_4.6H_2O$ | 0.5 nM |
| $SnCl_2.2H_2O$ | 0.5 nM |
| Gentamicin | 50 µg/ml |

The conditioned medium was isolated from high density monolayer cultures of HepG2 hepatoblastoma cells (American Type Tissue Collection #HB80–65) after 72 hours of cultivation. This conditioned medium is added to normal HGM at a 35% concentration. (Alternatively, human liver epithelial cells transformed by transfection with SV40 DNA (NCI/NIH, patent pending) in contact with HGM may be used instead of HepG2.

EXAMPLE 3 (NORMAL CELLS)

Isolation of hepatocytes: Human hepatocytes were isolated by a combination of perfusion and digestion as previously described. Upon removal of human livers, the tissue was kept in ice cold L-15 medium and transported to the site of liver cell isolation. The hepatocytes were dissociated into cell suspensions by perfusing the liver with a calcium and magnesium free Hank's balanced salt solution containing 0.5 mM EDTA, and 0.05M Hepes at 37° C., at a flow rate of 30–40 ml/min for 15 min.

The perfusate was then changed to a digestion solution containing collagenase (185–200 U/ml) at 37° C. at a flow rate of 30–40 ml/min for 20 min. The dissociated hepatocytes were purified from debris and red blood cells by 3 successive washes with L-15 and filtration through a 10µ nylon filter. The hepatocytes were suspended in Waymouth's medium supplemented with 10% fetal bovine serum (FBS), 1 µg/ml insulin and 50 µg/ml gentamicin. The yield estimated counting the cells with a hemocytometer were $1-2\times10^7$ cells/g of liver tissue. Over 90% of the hepatocytes excluded trypan blue.

Primary culture of human hepatocytes: Following isolation, all hepatocytes were seeded into collagen coated flasks (Flow Lab, Rockville, Md.) in T-75 tissue culture flasks (Lux, Miles Scientific, Napperville, Ill.) at a density of $5\times10^5$ cells/flask. All flasks were maintained in a humidified 3.5 humidified incubator at 37° C. Twenty-four hrs after isolation, the medium was changed to a semidefined serum-free medium consisting of a basal medium PFMR4 made without arginine and supplemented with ornithine (2 mM), insulin (10 µg/ml), hydrocortisone (0.2 µM), epidermal growth factor (5 ng/ml), transferrin (10 µg/ml), phosphoethanolamine (0.5 µM), cholera toxin (25 ng/ml), triiodothyronine (10 nM), bovine pituitary extract (7.5 µg/ml) and factor-free serum (10%). After two weeks, this medium was supplemented (35%) with conditioned medium obtained by placing the medium described above in contact with high density cultures of human hepatoblastoma cell line (HepG2) for 72 hrs.

These cells continued to proliferate slowly for about 15 weeks at which time the culture scenesced. The original culture was subcultured four times and the cells underwent approximately 12 replications.

These cells were keratin positive and 20% retained the ability to produce albumin as demonstrated by immunocytochemistry.

What is claimed is:

1. A cell culturing medium suitable for primary culture of normal human hepatocytes comprising the following ingredients:

an effective amount of ornithine to allow proliferation of human hepatocytes;

an effective cell growth promoting amount of growth factor inactivated serum;

retinoic acid at concentration of 1 to 300 nM;

an effective amount of calcium ions, which is represented by a concentration from 0.2 to 1 mM, high enough to promote human hepatocyte cell growth but low enough to avoid the inducement of terminal cellular differentiation;

an effective cell growth promoting amount of glucose;

an effective amount of insulin to aid cells in glucose uptake;

an effective cell growth promoting amount of hydrocortisone;

an effective amount of epidermal growth factor to bind epidermal growth factor receptor on cells;

an effective amount of transferrin to increase DNA synthesis in cells;

an effective amount of cholera toxin to increase DNA synthesis in cells;

an effective amount of triiodothyronine to increase DNA synthesis in cells;

an effective growth promoting amount of mammalian hormones; and an effective cell growth promoting amount of lipoprotein, cholesterol, phospholipids and fatty acids, wherein said medium contains no arginine and has a low endotoxin concentration, thereby providing a culture medium which supports the growth of normal human hepatocyte cells and does not support the growth of fibroblast cells.

2. A method for selectively culturing normal adult human liver epithelial cells, which comprises: providing a primary tissue culture from the liver of an adult human; and culturing said primary tissue culture in the cell culturing medium of claim 1.

3. A cell culturing medium for primary culture of normal human hepatocytes which comprises:
an effective amount of ornithine to allow proliferation of human hepatocytes;
an effective cell growth promoting amount of growth factor inactivated serum;
an effective cell growth promoting amount of the essential amino acids except arginine;
an effective growth promoting amount of water soluble vitamins;
an effective cell growth promoting amount of coenzymes;
an effective cell growth promoting amount of sodium ions;
an effective cell growth promoting amount of calcium ions;
an effective cell growth promoting amount of glucose;
an effective amount of insulin to aid cells in glucose uptake;
an effective cell growth promoting amount of hydrocortisone;
an effective amount of epidermal growth factor to bind epidermal growth factor receptor on cells;
an effective amount of transferrin to increase DNA synthesis in cells;
an effective amount of cholera toxin to increase DNA synthesis in cells;
an effective amount of triiodothyronine to increase DNA synthesis in cells;
an effective amount of retinoic acid to increase DNA synthesis in cells, said amount resulting in a concentration of 1 to 300 nM;
an effective growth promoting amount of mammalian hormones; and an effective cell growth promoting amount of lipoprotein, cholesterol, phospholipids and fatty acids, wherein said medium contains no arginine and has a low concentration of endotoxin, thereby providing a medium which supports the growth of normal human hepatocyte cells and does not support the growth of fibroblast cells.

4. A method for selectively culturing normal adult human liver epithelial cells, which comprises: providing a primary tissue culture from the liver of an adult human; and culturing said primary tissue culture in the cell culturing medium of claim 3.

5. An aqueous cell culturing medium suitable for primary culture of normal human hepatocytes which comprises:
water;
an effective amount of ornithine to allow proliferation of human hepatocytes;
an effective cell growth promoting amount of growth factor inactivated serum;
an effective cell growth promoting amount of all of the essential amino acids, except arginine;
an effective cell growth promoting amount of water soluble vitamins;
an effective cell growth promoting amount of coenzymes;
an effective cell growth promoting amount of sodium ions;
an effective amount of calcium ions, which is represented by a concentration from 0.2 to 1 mM, high enough to promote human hepatocyte growth but low enough to avoid the inducement of cellular differentiation;
an effective cell growth promoting amount of glucose;
insulin in an amount of 1 to 10 $\mu$g/ml;
hydrocortisone in an amount of 0.05 to 1 $\mu$M;
epidermal growth factor in an amount of 1 to 25 ng/ml;
transferrin in an amount of 1 to 10 $\mu$g/ml;
cholera toxin in an amount of 5 to 50 ng/ml;
triiodothyronine in an amount of O1 to 100 nM;
retinoic acid in an amount of 1 to 30 nM;
an effective amount of mammalian pituitary extract to provide hormones and mitogenic factors necessary for culturing human hepatocytes;
an effective cell growth promoting amount of lipoprotein, cholesterol, phospholipids and fatty acids;
an effective cell growth promoting amount of conditioned medium derived from HepG2 hepatoblastoma cells or a mutant of said HepG2 cells; and
an effective amount of a buffer to maintain the pH of the medium between 6.7 and 7.6, wherein said medium contains no arginine and has a low concentration of endotoxin, thereby providing a medium which supports the growth of normal human hepatocyte cells and does not support the growth of fibroblast cells.

6. The medium of claim 5, wherein said pituitary extract is bovine pituitary extract.

7. The medium of claim 5, which contains 100 to 700 $\mu$g/ml of a mixture of lipoprotein, cholesterol, phospholipids, and fatty acids with low endotoxin.

8. A method for selectively culturing normal adult human liver epithelial cells, which comprises: providing a primary tissue culture from the liver of an adult human; and culturing said primary tissue culture in the cell culturing medium of claim 5.

9. An aqueous cell culturing medium suitable for primary culture of normal human hepatocytes which comprises:
   water;
   an effective cell growth promoting amount of all of the essential amino acids, except arginine;
   an effective cell growth promoting amount of growth factor in activated serum;
   an effective growth promoting amount of water soluble vitamins;
   an effective cell growth promoting amount of coenzymes;
   an effective cell growth promoting amount of sodium ions;
   calcium ions in a concentration of 0.2 to 1 mM;
   an effective cell growth promoting amount of glucose;
   insulin in an amount of 1 to 10 µg/ml;
   hydrocortisone in an amount of 0.05 to 1 µM;
   epidermal growth factor in an amount of 1 to 25 ng/ml;
   transferrin in an amount of 1 to 10 µg/ml;
   cholera toxin in an amount of 5 to 50 ng/ml;
   triiodothyronine in an amount of 1 to 100 nM;
   retinoic acid in an amount of 1 to 300 nM;
   an effective amount of mammalian pituitary extract to provide hormones and mitogenic factors necessary for culturing normal adult human liver epithelial cells;
   an effective cell growth promoting amount of conditioned medium derived from HepG2 hepatoblastoma cells or a mutant of said HepG2 cells; and
   100–700 µg/ml of a mixture of lipoprotein, cholesterol, phospholipids, and fatty acids with low endotoxin; and an effective amount of a buffer to maintain the pH of the medium between 6.7 and 7.6,
   wherein said medium contains no arginine, thereby providing a medium which supports the growth of normal human hepatocyte cells but does not support the growth of fibroblast cells.

10. A method for culturing normal adult human liver epithelial cells, which comprises: culturing normal adult human liver epithelial cells in the cell culturing medium of claim 9.

11. The method of claim 10, wherein said cells are cultured for at least 10 rounds of DNA synthesis.

12. A mammalian cell culturing medium, consisting essentially of:
   an effective amount of ornithine to allow proliferation of human hepatocytes;
   an effective amount of growth factor inactivated serum;
   retinoic acid in an amount of 1 to 300 nm; and
   calcium ions in an amount of 0.2 to 1 mM, wherein said medium contains essentially no arginine.

13. The cell culturing medium of claim 12, wherein said growth factor inactivated serum is chemically denatured serum.

14. A cell culturing medium suitable for primary culture of normal human hepatocytes comprising the following ingredients:
   an effective amount of ornithine to allow proliferation of human hepatocytes;
   an effective cell growth promoting amount of growth factor inactivated serum;
   retinoic acid at a concentration of 1 to 300 nM;
   an effective amount of calcium ions, which is represented by a concentration from 0.2 to 1 mM, high enough to promote human hepatocyte growth but low enough to avoid the inducement of cellular differentiation;
   an effective cell growth promoting amount of glucose;
   an effective amount of insulin to aid cells in glucose uptake;
   an effective cell growth promoting amount of hydrocortisone;
   an effective amount of epidermal growth factor to bind epidermal growth factor receptor on cells;
   an effective amount of transferrin to increase DNA synthesis in cells;
   an effective amount of cholera toxin to increase DNA synthesis in cells;
   an effective amount of triiodothyronine to increase DNA synthesis in cells;
   an effective amount of triiodothyronine to increase DNA synthesis in cells;
   an effective amount of mammalian hormones; and
   wherein said medium contains no arginine, thereby providing a medium which supports the growth of normal human hepatocyte cells but does not support the growth of fibroblast cells.

15. A cell culturing medium suitable for primary culture of normal human hepatocytes which comprises:
   an effective amount of ornithine to allow proliferation of human hepatocytes;
   an effective cell growth promoting amount of growth factor inactivated serum;
   an effective cell growth promoting amount of the essential amino acids, except arginine;
   an effective growth promoting amount of water soluble vitamins;
   an effective cell growth promoting amount of coenzymes;
   an effective cell growth promoting amount of sodium ions;
   an effective cell growth promoting amount of calcium ions;
   an effective cell growth promoting amount of glucose;
   an effective amount of insulin to aid cells in glucose uptake;
   an effective cell growth promoting amount of hydrocortisone;
   an effective amount of epidermal growth factor to bind epidermal growth factor receptor on cells;
   an effective amount of transferrin to increase DNA synthesis in cells;
   an effective amount of cholera toxin to increase DNA synthesis in cells;
   an effective amount of triiodothyronine to increase DNA synthesis in cells;
   an effective amount of retinoic acid to increase DNA synthesis in cells, said amount resulting in a concentration of 1 to 300 nM;
   an effective growth promoting amount of mammalian hormones;
   wherein said medium contains no arginine, thereby providing a medium which supports the growth of normal human hepatocyte cells but does not support the growth of fibroblast cells.

* * * * *